US00PP26244P2

(12) United States Plant Patent
Hooijman

(10) Patent No.: US PP26,244 P2
(45) Date of Patent: Dec. 22, 2015

(54) ROSE PLANT NAMED 'ESM R071'

(50) Latin Name: *Rosa hybrida*
Varietal Denomination: ESM R071

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 148 days.

(21) Appl. No.: 13/987,858

(22) Filed: Sep. 9, 2013

(51) Int. Cl.
*A01H 5/02* (2006.01)

(52) U.S. Cl.
USPC ..... Plt./145

(58) Field of Classification Search
USPC ..... Plt./145
See application file for complete search history.

(56) References Cited

PUBLICATIONS

UPOV hit on Rose plant named 'ESM R071', QZ PBR 20112028, published Oct. 15, 2011.*
CPVO application for *rosa* 'ESM R071', published Oct. 15, 2011.*
PVP Detail for *rosa* 'ESM R071', published Oct. 15, 2011.*

* cited by examiner

*Primary Examiner* — Anne Grunberg
(74) *Attorney, Agent, or Firm* — C. A. Whealy

(57) ABSTRACT

A new and distinct cultivar of Rose plant named 'Esm R071', characterized by its upright and strong flowering stems; vigorous growth habit and high productivity; freely flowering habit; dark yellow-colored flowers that are typically grown as spray types; excellent postproduction longevity; and tolerance to *Botrytis*, powdery mildew, downy mildew and spider mites.

1 Drawing Sheet

Botanical designation: *Rosa hybrida.*
Cultivar denomination: 'ESM R071'.

CROSS-REFERENCED TO CLOSELY-RELATED APPLICATIONS

Applicant: Aloysius A. J. Hooijman
Title: Rose Plant Named 'ESM R073'
Filed: Sep. 9, 2015
Application Number: U.S. Plant patent application Ser. No. 13/987,855

BACKGROUND OF THE INVENTION

The present Invention relates to a new and distinct cultivar of Rose plant, botanically known as *Rosa hybrida*, commercially used as a cut flower Rose plant, typically referred to as a floribunda type, and hereinafter referred to by the name 'Esm R071'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in July, 2007 of a proprietary Rose selection identified as Line 369, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2009.

Asexual reproduction of the new Rose plant by bud grafting in El Quinche, Pichincha, Ecuador since October, 2009 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without however, any variance in genotype.

The following traits have been repeatedly observed and are determined to be the unique characteristics of 'Esm R071'. These characteristics in combination distinguish 'Esm R071' as a new and distinct Rose plant:

1. Upright and strong flowering stems.
2. Vigorous growth habit and high productivity.
3. Freely flowering habit.
4. Dark yellow-colored flowers that are typically grown as spray types.
5. Excellent postproduction longevity.
6. Tolerant to *Botrytis*, powdery mildew, downy mildew and spider mites.

Plants of the new Rose differ from plants of the female parent selection in the following characteristics:

1. Plants of the new Rose are taller than plants of female parent selection.
2. Stems of plants of the new Rose have slightly more thorns than stems of plants of the female parent selection.

3. Flowers of plants of the new Rose have more petals than flowers of plants of the female parent selection.
4. Plants of the new Rose and the female parent selection differ in flower color as plants of the female parent selection have light red-colored flowers.

Plants of the new Rose differ from plants of the male parent selection in the following characteristics:

1. Plants of the new Rose are slightly shorter than plants of the male parent selection.
2. Stems of plants of the new Rose have slightly more thorns than stems of plants of the male parent selection.
3. Flowers of plants of the new Rose have more petals than flowers of plants of the male parent selection.
4. Flower buds and flowers of plants of the new Rose are larger than flower buds and flowers of plants of the male parent selection.

Plants of the new Rose can be compared to plants of Rose 'Yellow Babe', not patented. In side-by-side comparisons conducted in El Quinche, Pichincha, Ecuador, plants of the new Rose differed from plants of 'Yellow Babe' in the following characteristics:

1. Plants of the new Rose were slightly shorter than plants of 'Yellow Babe'.
2. Plants of the new Rose were more vigorous than plants of 'Yellow Babe'.
3. Plants of the new Rose had stronger stems than plants of 'Yellow Babe'.
4. Stems of plants of the new Rose had more thorns than stems of plants of 'Yellow Babe'.
5. Plants of the new Rose had larger leaflets than plants of 'Yellow Babe'.
6. Plants of the new Rose had taller and broader flower sprays than plants of 'Yellow Babe'.
7. Plants of the new Rose flower about four days later than plants of 'Yellow Babe'.
8. Plants of the new Rose had larger flower buds and flowers than plants of 'Yellow Babe'.
9. Flowers of plants of the new Rose had more petals than flowers of plants of 'Yellow Babe'.
10. Flowers of plants of the new Rose were darker yellow than flowers of plants of 'Yellow Babe'.

Plants of the new Rose can also be compared to plants of *Rosa hybrida* 'Esm R073', disclosed in U.S. Plant patent application Ser. No. 13/987,855, primarily in flower color as plants of 'Esm R073' have orange-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of typical flowering stem of 'Esm R071'.

The photograph at the upper right of the sheet is a close-up view of a typical flowering stem of 'Esm R071'.

The photograph at the lower left of the sheet is a close-up view of a typical flower of 'Esm R071'.

The photograph at the lower right of the sheet are close-up views of the upper and lower surfaces of typical leaves of 'Esm R071'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in beds in a polyethylene-covered greenhouse in El Quinche, Pichincha, Ecuador and under typical hydroponic Rose production practices. Plants were pinched 13 to 14 weeks after planting and were 118 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm R071'.

Parentage:

*Female, or seed, parent*.—Proprietary seedling selection of *Rosa hybrida* identified Line 369, not patented.

*Male, or pollen, parent*.—Proprietary seedling selection of *Rosa hybrida* identified Line 222, not patented.

Propagation:

*Type*.—By bud grafting.

*Time to initiate roots*.—About seven to ten days at 26° C. to 30° C.

*Time to produce a rooted young plant*.—About four to five weeks at 22° C. to 26° C.

*Root description*.—Fibrous, fine; close to N199A in color.

*Rooting habit*.—Moderately freely branching; medium density.

Plant description:

*Plant and growth habit*.—Perennial shrub; upright and strong flowering stems; typically grown as a spray-type cut flower; vigorous growth habit.

*Branching habit*.—Freely basal branching habit; highly productive with about 8.4 to 9.6 flowering stems developing per plant per year.

*Plant height*.—About 127 cm.

*Plant width (spread)*.—About 59 cm.

*Lateral branches*.—Quantity: About 15 lateral branches develop per plant. Length: About 92 cm. Diameter: About 7 mm. Internode length: About 4.6 cm. Texture: Smooth, glabrous; older stems, woody. Color: Close to 146A. Thorns: Density: Medium. Shape: Triangular with sharp acuminate apices; slightly incurved and flat. Height: About 1 cm. Length, at base: About 9 mm. Color, immature: Close to 183A. Color, mature: Close to between 178A and 199A.

Leaf description:

*Arrangement*.—Alternate; compound with typically five to seven leaflets per leaf.

*Leaf length*.—About 15.3 cm.

*Leaf width*.—About 11.3 cm.

*Terminal leaflet length*.—About 6 cm.

*Terminal leaflet width*.—About 4.4 cm.

*Lateral leaflet length*.—About 5.5 cm.
*Lateral leaflet width*.—About 3.8 cm.
*Leaflet shape*.—Ovate.
*Leaflet apex*.—Acute.
*Leaflet base*.—Attenuate.
*Leaflet margin*.—Serrate.
*Leaflet texture, upper and lower surfaces*.—Smooth, glabrous; coriaceous.
*Leaflet venation pattern*.—Pinnate.
*Leaflet color*.—Developing leaflets, upper surface: Close to 139A; towards the margins, close to 187A. Developing leaflets, lower surface: Close to 146A. Fully expanded leaflets, upper surface: Close to 139A; venation, close to 146C. Fully expanded leaflets, lower surface: Close to 147B; venation, close to 146D.
*Petioles, leaves*.—Length: About 1.2 cm. Diameter: About 2 mm. Texture, upper surface: Prickly. Texture, lower surface: Smooth, glabrous. Color, upper surface: Close to 146A and 166A. Color, lower surface: Close to 146A to 146C.
*Petioles, leaflets*.—Length: About 1.7 cm. Diameter: About 1.2 mm. Texture, upper surface: Prickly. Texture, lower surface: Smooth, glabrous. Color, upper surface: Close to 146A. Color, lower surface: Close to 146A to 146C.
*Stipules*.—Arrangement and appearance: Two, adnate to the petiole, leafy in appearance. Length: About 2.7 cm. Width: About 2.1 mm. Shape: Roughly deltoid. Apex: Acuminate, tapered. Base: Tapered. Margin: Serrate. Texture, upper and lower surfaces: Irregularly pubescent; membranous. Venation pattern: Pinnate. Color, upper surface: Close to 137A. Color, lower surface: Close to 146A.

Flower description:
*Flower type and flowering habit*.—Symmetrical rosette flowers; flowers typically grown as spray types; flowers face upright.
*Flowering season*.—Plants of the new Rose flower year-round under greenhouse conditions; early flowering habit, plants begin flowering about 78 days after pinching; in the garden, optimal flowering from spring through autumn; flowering intermittent.
*Spray height*.—About 24 cm.
*Spray diameter*.—About 19 cm.
*Quantity of flowers per spray*.—About seven.
*Flower diameter*.—About 7.8 cm.
*Flower depth* (*height*).—About 3.3 cm.
*Flower longevity on plant*.—About 23 days; flowers persistent.
*Flower longevity as a cut flower*.—Excellent postproduction longevity, flowers last about ten to eleven days.
*Fragrance*.—Fragrant, pleasant.
*Flower buds*.—Shape: Ovoid. Length: About 3.1 cm. Diameter: About 2.2 cm. Color: Close to 144A.
*Petals*.—Quantity: About 40 to 45 per flower; petals imbricate. Length: About 2.9 cm. Width: About 2.9 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Close to 13A. When opening, lower surface: Close to 15A. Fully opened, upper surface: Close to 17B. Fully opened, lower surface: Close to 23A.
*Petaloids*.—Quantity: About six; petaloids whorled. Length: Variable. Width: Variable. Shape: Irregularly shaped. Apex: Blunt to shortly acute. Base: Obtuse. Margin: Entire or uneven. Texture, upper and lower surfaces: Smooth, glabrous; papery to coriaceous. Color: When opening and fully opened, upper surface: Close to 17A; towards the base, close to 153D. When opening and fully opened, lower surface: Close to 13A and 15A.
*Sepals*.—Quantity per flower: Typically five in a single whorl. Length: About 3.2 cm. Width: About 1 cm. Shape: Roughly deltoid. Apex: Tapered. Base: Truncate. Margin: Entire; glandular. Texture, upper surface: Pubescent; leathery. Texture, lower surface: Glandular along the margins; leathery. Color: When opening, upper surface: Close to 146B. When opening, lower surface: Close to 144A. Fully opened, upper surface: Close to 146C to 146D. Fully opened, lower surface: Close to 144A to 144B.
*Pedicels*.—Length: About 2.6 cm. Diameter: About 2.9 mm. Strength: Strong. Aspect: About 33° from vertical. Texture: Glandular. Color: Close to 146B and N199C.
Reproductive organs.—Stamens: Quantity: About 85 per flower. Anther length: About 2.8 mm. Anther shape: Reniform. Anther color: Close to 163B. Filament color: Close to 14A. Pollen amount: Scarce. Pollen color: Close to 163A to 163B. Pistils: Quantity: About 105 per flower. Pistil length: About 1.2 cm. Stigma shape: Broadly reniform. Stigma color: Close to 160A. Style length: About 8.7 mm. Style color: Close to 145D. Receptacle height: About 1.1 cm. Receptacle diameter: About 1 cm. Receptacle shape: Cup-shaped. Receptacle texture: Smooth, glabrous. Receptacle color: Close to 144A. Seeds and fruits: Seed and fruit development have not been observed on plants of the new Rose.

Pathogen & pest tolerance/resistance: Plants of the new Rose have been observed to tolerant to *Botrytis*, powdery mildew, downy mildew and spider mites. Plants of the new Rose have not been observed to be tolerant or resistant to other pathogens and pests common to Rose plants.

Temperature tolerance: Plants of the new Rose have been observed to tolerate temperatures ranging from 0° C. to 35° C.

It is claimed:

1. A new and distinct Rose plant named 'Esm R071' as illustrated and described.

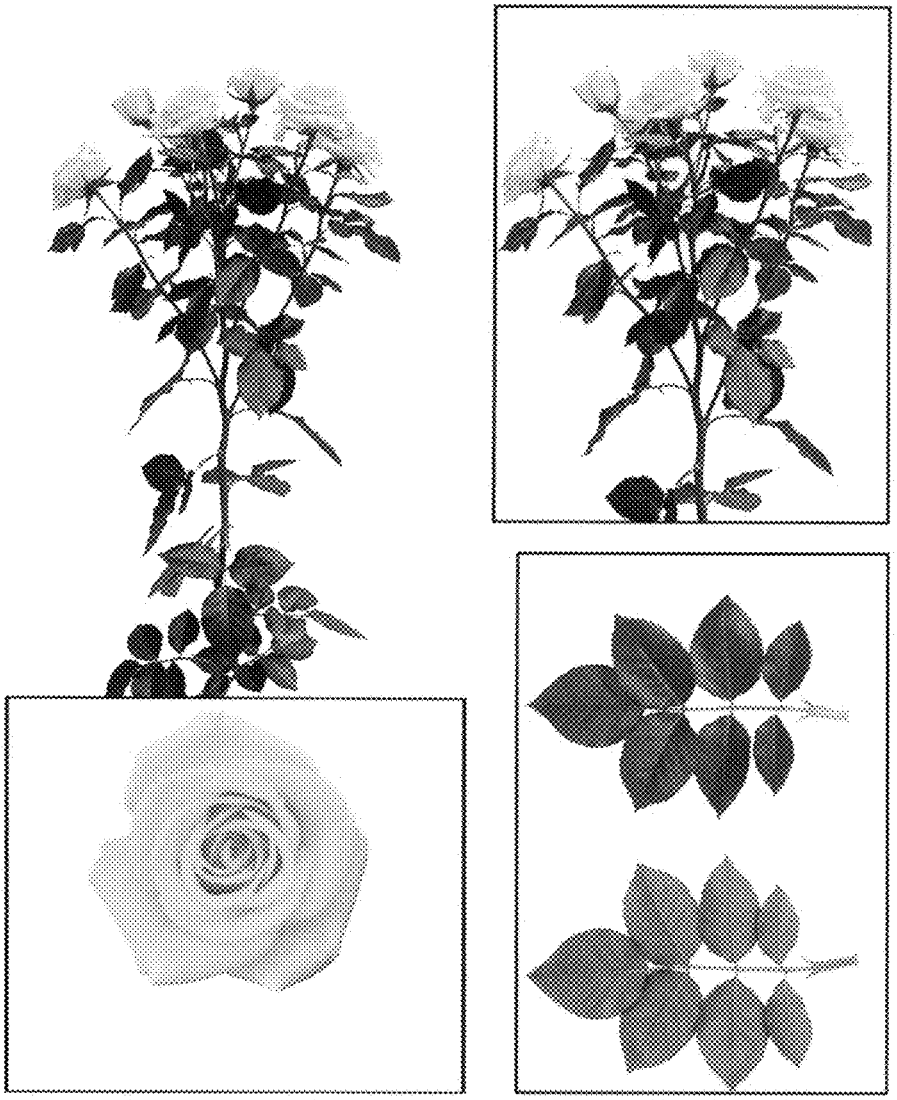

* * * * *